(12) United States Patent
Arstad et al.

(10) Patent No.: US 8,309,055 B2
(45) Date of Patent: Nov. 13, 2012

(54) PET RADIOTRACERS

(75) Inventors: Erik Arstad, London (GB); Edward George Robins, London (GB)

(73) Assignee: Hammersmith Imanet Limited, London (GB)

( * ) Notice: Subject to any disclaimer, the term of this patent is extended or adjusted under 35 U.S.C. 154(b) by 0 days.

(21) Appl. No.: 13/359,774

(22) Filed: Jan. 27, 2012

(65) Prior Publication Data

US 2012/0130122 A1 May 24, 2012

Related U.S. Application Data

(62) Division of application No. 12/097,831, filed as application No. PCT/NO2006/000482 on Dec. 15, 2006.

(30) Foreign Application Priority Data

Dec. 21, 2005 (GB) .................................. 0525949.4

(51) Int. Cl.
*A61K 51/00* (2006.01)
*A61M 36/14* (2006.01)

(52) U.S. Cl. ..................... 424/1.89; 424/1.11; 424/1.53; 424/1.65; 424/1.85; 565/444

(58) Field of Classification Search .................. 424/1.89
See application file for complete search history.

(56) References Cited

U.S. PATENT DOCUMENTS

| | | | |
|---|---|---|---|
| 5,998,624 | A | 12/1999 | Goodman |
| 6,096,874 | A | 8/2000 | Wallace et al. |
| 6,274,119 | B1 | 8/2001 | Barrio |
| 6,344,179 | B1 | 2/2002 | Goodman |
| 6,843,979 | B2 | 1/2005 | Goodman |
| 2005/0130235 | A1 | 6/2005 | Hsieh-Wilson et al. |

FOREIGN PATENT DOCUMENTS

| | | |
|---|---|---|
| WO | 99/11590 | 3/1999 |
| WO | 00/64490 | 11/2000 |
| WO | 2004/083195 | 9/2004 |
| WO | 2004/093650 | 11/2004 |
| WO | 2005/061415 | 7/2005 |
| WO | 2005/082425 | 9/2005 |
| WO | 2005/105159 | 11/2005 |
| WO | 2006/083424 | 8/2006 |
| WO | 2006/127024 | 11/2006 |

OTHER PUBLICATIONS

Nagatsugi, Fumi, et.al. "Synthesis of 20-(18F)fluoroarachidonic acid: a potential phospholipid metabolic agent" Journal of labeled Compounds and Radiopharmaceticals vol. 34, No. 12, 1994 pp. 1121-1127.

Yu, Chung-Shan, et.al. "Syntheses of 5-(2-radiohaloethyl)-and5-(2-radiohalovinyl)-2-deoxyu ridines. Novel types of radiotracer for monitoring cancer gene therapy with PET" Journal of Labelled Compounds and Radiopharmaceuticals, vol. 46, No. 5, Apr. 2003 pp. 421-439.

Dejusu, O.T., et.al. "Visualization of dopamine nerve terminals by positron tomography using fluorine-18 fluoro-beta-fluoromethylene-m-tyrosine" Brain Research, vol. 597, No. 1, 1992, pp. 151-154.

Van Der Linde, et.al. "The chemistry of 18F-recoil atoms in gaseous CF2H-CF2H scavenged with H2S" Radiochem. Radioanal Letter, 1981 vol. 49. pp. 239-250.

Manning, et.al. "Chemistry of nuclear recoil 18F atoms. 10. Studies of 18F caged capture processes in CH3CF3/H2S and CH3CHF2/H2S liquid mixtures" Journal of Physical Chemistry, 1977, vol. 81 pp. 2576-2586.

Iyer, et.al. "Thermal fluorine atom reactions with 3-chloropropene" Journal of Physical Chemistry, 1985, vol. 89, pp. 5051-5057.

Iyer, et.al. "Atom-transfer reaction rates for thermal fluorine atoms with CH3X and CF3X (X—Br, I)" Journal of Physical Chemistry, 1981, vol. 85 pp. 2493-2497.

GB0525949.4 Search Report dated Apr. 20, 2006.

PCT/NO2006/000482 Int'l search report/written opinion dated Apr. 2007.

*Primary Examiner* — Michael G Hartley
*Assistant Examiner* — Sean R Donohue
(74) *Attorney, Agent, or Firm* — Yonggang Ji

(57) ABSTRACT

The invention relates to novel $^{18}$F-labelled compounds which may be suitable for use as Positron Emission Tomography (PET) radiotracers, and to processes for preparation of such. The $^{18}$F-labelled compounds of the invention comprise a [$^{18}$F]fluoroalkenyl group.

7 Claims, No Drawings

PET RADIOTRACERS

This application is a divisional of U.S. patent application Ser. No. 12/097,831 filed June 17, 2008, abandoned, which a filing under 35 U.S.C. 371 of international application number PCT/NO2006/000482, filed Dec. 15, 2006, which claims priority to patent application number 0525949.4 filed in Great Britain on Dec. 21, 2005.

The invention relates to novel $^{18}$F-labelled compounds and their use as Positron Emission Tomography (PET) radiotracers, and to processes for preparation of such compounds. The invention further relates to kits for preparation of the compounds and to compositions comprising the $^{18}$F-labelled compounds.

The favoured radioisotope for PET, $^{18}$F, has a relatively short half-life of 110 minutes. $^{18}$F-labelled tracers for PET therefore have to be synthesised and purified as rapidly as possibly, and ideally within one hour of clinical use. PET tracers are frequently labelled with [$^{18}$F]fluoroalkyl groups to produce [$^{18}$F]fluoroalkylated PET tracers. [$^{18}$F]fluorohaloalkanes are important reagents for performing O—, N—, and S—[$^{18}$F]fluoroalkylations and are commonly used to radiolabel ligands for use in PET studies. Solid-phase preparations of [$^{18}$F]fluorohaloalkanes are described in WO-A-2004/056726.

The PET tracers comprising [$^{18}$F]fluoroalkyl groups may however suffer from in vivo defluorination wherein the [$^{18}$F] fluoride is cleaved off from the rest of the tracer. This may lead to decreased signal and increased background noise signal mainly from uptake of [$^{18}$F]fluoride in bone tissue. There is hence a clinical need for development of improved PET tracers which are more stable in vivo and there is a need for synthetic methods for their preparation in good radiochemical yield.

In view of these needs the present invention provides new compounds suitable as PET tracers. The compounds of the present invention provide an improved target/background signal ratio and increased specificity and sensitivity.

In a first aspect, the present invention provides a compound comprising a [$^{18}$F]fluoroalkenyl group. The compounds are suitable for use as PET radiotracers. The compound is labelled with $^{18}$F either in the 1- or 2-position of an alkenyl group, providing 1-[$^{18}$F]-fluoro-1-alkenylated and 2-[$^{18}$F]-fluoro-1-alkenylated compounds.

The compounds of the invention comprise a [$^{18}$F]fluoroalkenyl group, rather than a [$^{18}$F]fluoroalkyl group, used in the state of the art. It has been found that the compounds of the invention to a less degree undergo in vivo defluorination compared to fluoroalkylated compounds and improved specificity and an increased target/background signal ratio is achieved. Haloalkenes, i.e. compounds of the invention, cannot undergo an $S_N2$ substitution, and have therefore an increased resistance to dehalogenation, i.e. are more stable in vivo than the haloalkanes.

In one embodiment the invention provides $^{18}$F-labelled compounds of formula (I)

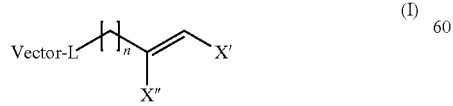

wherein
X' and X" are independently selected from hydrogen and $^{18}$F, with the proviso that either of X' or X" is a $^{18}$F-atom;

n is an integer from 1 to 5;
the vector comprises a moiety having affinity for a biological target; and
L represents a linker moiety.

A $^{18}$F-fluoroalkyl group of PET tracers of the state of the art can be substituted with a [$^{18}$F]fluoroalkenyl group to provide a $^{18}$F-labelled compound of the invention.

The vector comprises a moiety that has affinity to a biological target, preferably which accumulates in biological targets due to their biological and/or physiological properties and therefore can be used to visualize biological structures, functions and pathological processes.

The vector may be of synthetic or natural origin, and is preferably synthetic. The vector has the ability to direct the compound to a region of a given disease. Preferably, the vector has affinity for the target, such as a biological receptor, and preferably binds to this. On the one hand the vector should have a high affinity for the receptor, and on the other hand it should "stay" on the receptor as long as necessary. The receptors may be located in the vascular system, in the extracellular space, associated with cell membranes or located intracellularly.

The vector can generally be any type of molecule that has affinity for a biological target. All vectors that can be linked to the fluoroalkenyl group without loosing their affinity to the biological target are relevant. The vector should be physiologically acceptable and should preferably have an acceptable degree of stability. The vector may comprise biomolecules, preferably selected from the group consisting of peptides, peptoids/peptidomimetics and proteins; oligonucleotides, such as oligo-DNA or oligo-RNA fragments; oligosaccharides; lipid-related compounds; hormones; synthetic small drug-like molecules; inhibitors; antibodies and antibody fragments; and derivatives and mimetics thereof.

Vectors comprising a peptide may include linear or cyclic peptides, or combinations thereof. The peptides comprise from 1-150 amino acids and are preferably 3-100mer peptides, and more preferably 3-30mer peptides. By the term "cyclic peptide" is meant a sequence wherein two amino acids are bonded together by a covalent bond which may be a peptide or disulphide bond or a synthetic non-peptide bond such as a thioether, phosphodiester, disiloxane or urethane, forming a cyclic bridge (ring). The peptides may comprise 1, 2 or more such cyclic bridges and the number of amino acids between two amino acids which are bonded are e.g. 3-15.

Suitable peptides for use in the vector include the following, using standard symbols for the amino acids:
somatostatin, octreotide and analogues;
peptides which bind to the ST receptor, where ST refers to the heat-stable toxin produced by *E. coli* and other micro-organisms;
laminin fragments e.g. YIGSR, PDSGR, IKVAV, LRE and KCQAGTFALRGDPQG;
N-formyl peptides for targeting sites of leukocyte accumulation;
Platelet factor 4 (PF4) and fragments thereof;
RGD-containing peptides;
Angiotensin II;
Endothelins;
Cytokines such as VEGF, EGF, hepatocyte growth factor, nerve growth factor, interferons, interleukins, platelet-derived growth factor, tumour necrosis factor, macrophage colony-stimulating factor and fragments thereof;
Chemokines such as MCP-1 and eotaxin;
Peptide fragments of $\alpha_2$-antiplasmin, fibronectin or beta-casein, fibrinogen or thrombospondin.

Synthetic peptides of the vector may be obtained by conventional solid phase synthesis, as described by Merrifield employing an automated peptide synthesizer (J. Am. Chem. Soc., 85: 2149 (1964)).

Suitable oligonucleotides in a vector comprising oligonucleotides are polymers of ribonucleotides or deoxyribonucleotides comprising between 5 and 100 units, preferably between 10 and 30 units. The oligonucleotides may contain only the five common nitrogen bases of natural nucleic acids, or they may contain non-natural and/or synthetic bases.

Suitable oligosaccharides in a vector comprising oligosaccharides are polymers of sugars, containing from three to twenty units, preferably from three to ten units. The constituent sugars are glucose, galactose, mannose, fructose, N-acetylglucosamine, N-acetylgalactosamine or sialic acids, but other sugars, including synthetically modified sugars, may be present. The sugar chains may be linear or branched.

Suitable lipid-related compounds in a vector comprising lipid-related compounds are hydrophobic compounds preferably from common building blocks of eukaryotic biological membranes, such as phospholipids, glycolipids or cholesterol. Preferably, they are related to or derived from these compounds. Examples of compounds that are derived from arachidonic acid are prostaglandins and thromboxanes. From phospholipids are derived lysophosphatidylcholine, diacylglycerol and platelet-activating factor; from cholesterol, steroids such as cortisol, progesterone, estradiol and testosterone. Retinoids also belong in this general class of compounds.

Suitable inhibitors enzyme, such as enzyme inhibitors, in a vector comprising inhibitors may be naturally occurring proteins such as cystatins, serpins or tissue inhibitors of metallo proteinases (TIMPs, native or modified). They may be of microbial origin, such as leupeptin, semi-synthetic, or synthetic, such as lysine chloromethyl ketone.

Suitable monoclonal antibodies or fragments thereof, in vectors comprising such antibodies, include: antibodies to the CD-20 antigen expressed on the surface of B-cells; anti-leucocyte or anti-granulocyte antibodies; anti-myosin antibodies or antibodies to carcinoembryonic antigen (CEA).

Suitable synthetic small drug-like molecules, in vectors comprising synthetic small drug-like molecules, include, but are not limited to: estradiol, estrogen, progestin, progesterone and other steroid hormones; ligands for the dopamine D-1 or D-2 receptor, or dopamine transporters such as tropanes; and ligands for the serotonin receptor.

In a preferred embodiment, the compounds of the invention comprise a linker, L, connecting the vector to the fluoroalkenyl moiety. In its simplest form L is a covalent bond or comprises a functional group which permits facile conjugation of the vector and the fluoroalkenyl moiety. L preferably comprises moieties selected from the group consisting of amines, amides, thioethers, ethers, sulfones, sulfoxides, sulfides, polyalkyleneglycols, polylactic acids or polyglycolic acid moieties and amino acids, e.g. peptides of 1 to 5 amino acids.

Compounds including a $^{18}$F-fluoroalkyl group, described for use as PET tracers, exist. Examples of such compounds include, but is not restricted to, benzothiazoles, 2-(1,1-dicyanopropen-2-yl)-6-(2-fluoroethyl)methylamino)-naphthalene (FDDNP), the halophenyl nortropane family and the 4-haloethenylphenyl tropane family (U.S. Pat. No. 6,843,97) In one embodiment, the invention provides similar compounds to these groups of compounds, but comprising a $^{18}$F-fluoroalkenyl moiety instead of a $^{18}$F-fluoroalkyl group. Preferred such compounds are described in the following.

Alzheimer's Disease is a neurodegenerative illness characterised by memory loss and other cognitive deficits. Amyloid-containing neuritic plaques are a prominent feature of selective areas of the brain in Alzheimer's Disease. In one embodiment the invention provides novel benzothiazole based compounds which may be used according to the methods described in WO-A-02/1333 and WO-A-04/083195 for in vivo imaging of amyloid in brain parenchyma. In this embodiment the invention provides benzothiazole based compounds of formula (IIa)

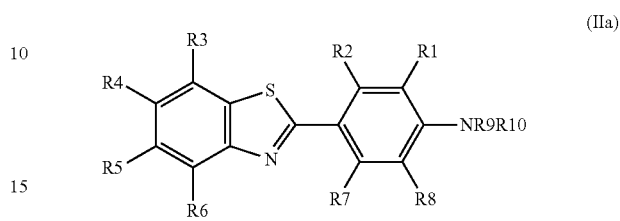

(IIa)

wherein R1 to R8 are independently selected from hydrogen, halogen, $C_{1-6}$ alkyl, $C_{1-6}$ haloalkyl, $C_1$-$C_6$-hydroxyalkyl, $C_1$-$C_6$-haloalkoxy, hydroxyl, cyano and nitro;

R9 and R10 are independently selected from hydrogen, $C_1$-$C_6$-alkyl, $C_1$-$C_6$-hydroxyalkyl and $C_1$-$C_6$-haloalkyl, $C_2$-$C_6$-alkenyl and $C_2$-$C_6$-alkynyl; and wherein one of the groups R1 to R10 comprises a group of formula (IIb)

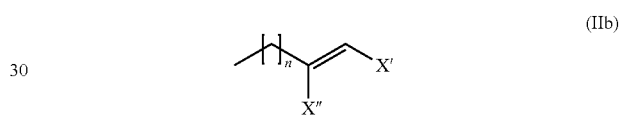

(IIb)

wherein X', X" and n are as defined in formula I.

Preferably, R9 or R10 comprises the group of formula (IIb).

A preferred compound according to this embodiment is provided by formula (IIc).

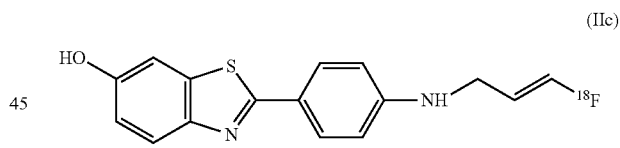

(IIc)

The various benzothiazole compounds of the invention may have utility as PET tracers in imaging of Alzheimers Disease.

In a further embodiment, the invention provides a compound of formula (III)

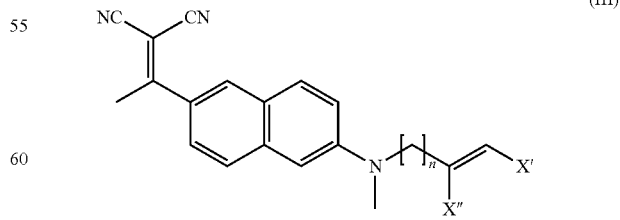

(III)

wherein

X', X" and n are as defined in formula I. The compounds of formula III are similar to 2-(1,1-dicyanopropen-2-yl)-6-(2- fluoroethyl)methylamino)naphthalene (FDDNP), but comprise a fluoroalkenyl group instead of a 2-fluoroethyl group.

In a yet further embodiment, the invention provides compounds which are fluoroalkenyl derivatives of 1-(2-chlorophenyl)-N-methyl-N-(1-methylpropyl)-3-isoquinolinecarboxyamide (PK 11195). PK 11195 and its preparation is disclosed e.g. in U.S. Pat. No. 5,998,624.

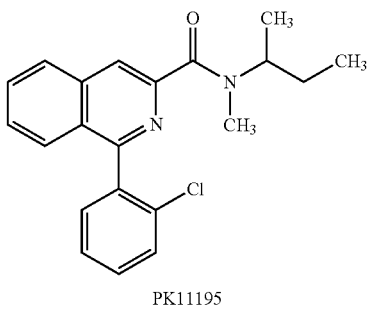

PK11195

The compounds of this embodiment have affinity to the peripheral benzodiazepine receptors (PBR) widely distributed throughout the body and which has been associated with numerous biological functions. PBR is involved in the regulation of apoptosis, in the regulation of cell proliferation, stimulation of steroidogenesis, immunomodulation, porphyrin transport, heme biosynthesis, anion transport and regulation of mitochondrial functions.

The preferred compounds of this embodiment are identified by formula (IV)

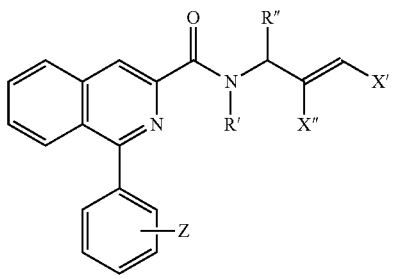

wherein

X' and X" are defined as in formula (I);

R' and R" are individually selected from hydrogen and lower alkyl, preferably $C_1$-$C_6$-alkyl groups, and more preferably methyl;

Z represents a halogen atom, preferably chloride, fluoride or bromide, and more preferably chloride.

Z is positioned in the ortho, meta or para position to the N-containing heteroaryl group and more preferably in the ortho position.

The compounds of formula IV may have utility as PET tracers in in vivo imaging of inflammations.

A preferred compound is identified by formula V:

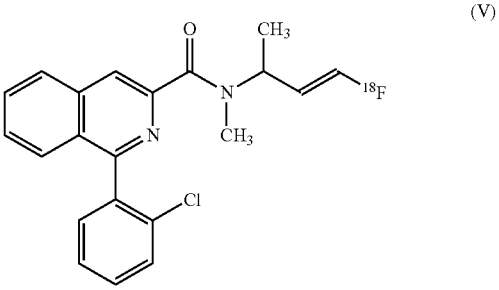

Viewed from a further aspect the invention provides processes for preparation of a compound according to the invention comprising a [$^{18}$F]fluoroalkenyl group. In one embodiment, the compounds of the present invention are prepared by a process based on iodonium chemistry. It has been found that a process comprising fluorinating an iodonium salts incorporating an alkene group and an aryl group, i.e. fluorinating an alkenyl(aryl)iodonium salt with $^{18}$F-fluoride, provides fluorinated alkenes with very high selectivity over the corresponding fluoroaryls.

The process for preparation of the compounds of the invention by iodonium chemistry preferably comprises fluorinating an alkenyl(aryl)iodonium salt of formula (VI),

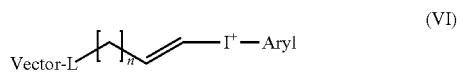

wherein

I$^+$-Aryl represents a phenyliodonium salt, wherein the aryl group is optionally substituted with methoxy, ethoxy, propyloxy, tert-butyloxy, halides or $C_1$-$C_6$-alkyl groups; and the vector, L and n are defined as in formula I.

The process for preparation of the alkenyl(aryl)iodonium salt of formula (VI) preferably comprises the further steps of:

i) reacting a vector moiety, optionally comprising a protecting group, comprising a functional group, with an alkyne comprising a leaving group, to prepare a compound comprising a vector moiety linked to an alkyne group;

ii) hydrometalating the alkyne group of the compound from step (i) to prepare a metalated alkene;

iii) reacting the metalated alkene of step (ii) with an iodonium transfer reagent to prepare the alkenyl(aryl)iodonium salt.

To prepare a compound of the invention the next step (iv) is fluorinating the alkenyl(aryl)iodonium salt from step (iii) with $^{18}$F-fluoride as disclosed.

The process of preparation is further outlined in Scheme 1.

Scheme 1

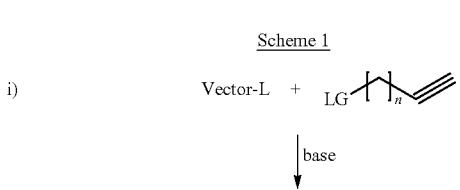

base

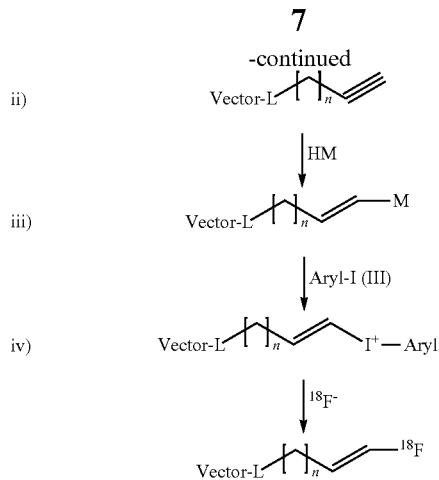

In step i) L represents a linker as defined for formula (I), comprising a functional group, which is preferably a good nucleophile, such as a group comprising an N, O or S atom, e.g. a group selected from a primary or secondary amine, —SH or OH group. LG represents a leaving group e.g. selected from chloride (Cl), bromide (Br), iodide (I), mesylate (OMs), tosylate (OTs), triflate (OTf) or nosylate (ONs). The base is e.g. selected from trialkylamines, pyridine, dimethylpyridine, potassium or sodium tertbutyloxide, sodium hydride, sodium hydroxide, potassium hydroxide, potassium carbonate or lithium diisopropyl amide (LDA). The reaction is preferably carried out in the presence of a suitable solvent, such as acetonitrile or acetone.

In step ii) M comprises a metal group and HM preferably represents a boron, silicon or tin reagent, such as catecholborane, wherein the hydrometalation of the alkyne group of the reaction product from step (i) will furnish a 1-boryl, 1-stannyl or a 1-silyl alkene. Alternatively, the metal can be a transition metal such as Pd that inserts directly into the alkyne group. Conversion from Pd etc. can be achieved by addition of a tin compound such as R'''$_3$SnSnR'''$_3$ or R'''$_3$SnCl, wherein R''' is an alkyl group preferably methyl or butyl. For the metalated alkene generated in this step the metal group M may be positioned either in the 1- or 2-position of the alkenyl group, depending on the conditions used.

In step iii) Aryl-I (III) represents a suitable iodonium transfer reagent, preferably a trivalent phenyliodonium salt, wherein the aryl group is optionally substituted with methoxy, ethoxy, propyloxy, tertbutyloxy, halides or $C_{1-6}$ alkyl groups. The iodonium transfer reagent is e.g. selected from Ph-I(OCOCH$_3$)$_2$, the Stang reagent of formula PhI(CN)OTf or Koser's reagent of formula Ph-I(OH)OTs. The generated alkenyl(aryl)iodonium salt may be precipitated or crystallised from solution, e.g. by addition of a non-polar solvent, such as n-hexane.

In step iv) the alkenyl(aryl)iodonium salt prepared in step (iii) is fluorinated with $^{18}F^-$. Fluorination with $^{18}F^-$ may be effected by treatment with any suitable source of $^{18}F^-$, such as Na$^{18}$F, K$^{18}$F, Cs$^{18}$F, tetraalkylammonium $^{18}$F fluoride, or tetraalkylphosphonium $^{18}$F fluoride. Depending on whether the metalated alkene generated in step iii) comprises a metal group in the first or second position of the alkenyl, a 1-fluoroalkenylated or a 2-fluoro-alkenylated compound is generated. To increase the reactivity of the fluoride, a phase transfer catalyst such as an aminopolyether or crown ether, for example, 4,7,13,16,21,24 hexaoxa-1,10-diazabicyclo[8,8,8] hexacosane (Kryptofix 2.2.2.) may be added and the reaction performed in a non protic solvent. Optionally, a free radical trap may be used to improve fluoridation yields, as described in WO-A-2005/061415. The "free radical trap" is an agent that interacts with free radicals and inactivates them. A suitable free radical trap for this purpose may be selected from 2,2,6,6-Tetramethylpiperidine-N-Oxide (TEMPO), 1,2-diphenylethylene (DPE), ascorbate, para-amino benzoic acid (PABA), α-tocopherol, hydroquinone, di-t-butyl phenol, β-carotene and gentisic acid. Preferred free radical traps for use in the process of the invention are TEMPO and DPE, with TEMPO being most preferred.

The treatment with $^{18}F^-$ is suitably effected in the presence of a suitable organic solvent such as acetonitrile, dimethylformamide, dimethylsulfoxide, tetrahydrofuran, dioxane, 1,2 dimethoxyethane, sulfolane, N-methylpyrrolidine, at a temperature of for example 15° C. to 180° C., preferably at elevated temperature, such as 80° C. to 150° C., for example around 120° C. On completion of the reaction, the $^{18}$F-labelled compound of the invention dissolved in the solvent may be separated from the solvent by evaporation and/or filtration, alternatively the product mixture is diluted with water, the product concentrated on a C18 cartridge and the product purified by HPLC prior to evaporation.

Any excess $^{18}F^-$ may be removed from the solution of the compound of the invention by any suitable means, for example by ion-exchange chromatography or solid phase absorption. Suitable ion-exchange resins include BIO-RAD AG 1-X8 or Waters QMA and suitable solid phase absorbents include alumina. The excess $^{18}F^-$ may be removed using such solid phases at room temperature in aprotic solvents. Any organic solvent may be removed by any standard method such as by evaporation at elevated temperature in vacuo or by passing a stream of inert gas such as nitrogen or argon over the solution.

In some cases, it may be necessary to protect functional groups in the vector to avoid unwanted reactions during the radiolabelling process. The process hence optionally includes a first step of protecting functional groups, such as amine groups or hydroxyl groups, in the vector moiety. Such protection may be achieved using standard methods of protecting group chemistry. After the radiolabelling with $^{18}$F is complete, any protecting groups may be removed by methods known in the art. Suitable protection and deprotection methodologies may be found, for example, in Protecting Groups in Organic Synthesis, Theodora W. Greene and Peter G. M. Wuts, published by John Wiley & Sons Inc. For example, any amine functionality in the vector may be protected by esters, suitably $C_{1-6}$ alkyl or $C_{1-6}$ haloalkyl esters, preferably acyl esters such as tert-butoxycarbonyl (Boc), or ethers, preferably $C_1$-$C_6$-alkyl ethers, or as amides suitably alkylamides such as formyl amide. A hydroxyl group in the vector may be protected as an ether, such as a silyl ether or alkyl ether, or as an ester. These protecting groups may be conveniently removed by hydrolysis, for example in the presence of acid or base. Such deprotection may be effected using a solid supported acid or base catalyst that render the need for post deprotection neutralization unnecessary.

The process steps i) to iv) are hence optionally followed by
v) removal of excess $^{18}F^-$, for example by ion-exchange chromatography; and/or
vi) removal of any protecting groups; and/or
vii) removal of organic solvents; and/or
viii) formulation of the resultant $^{18}$F-labelled compound of the invention as an aqueous solution.

In another embodiment of this aspect, the invention provides a process for the preparation of a compound according to the invention, comprising a [$^{18}$F]fluoroalkenyl group, based on a cross metathesis reaction. This reaction includes the transalkylidenation of two terminal alkenes under release of ethene, catalyzed by ruthenium carbenoids (Grubbs Catalyst). The transalkylidenation allows the exchange of substituents between different olefins. The compound is prepared in a process reacting $^{18}$F-fluoroethene with a compound comprising a terminal alkene group in the presence of a Grubbs Catalyst. The compound comprising the terminal alkene group is preferably a vector moiety comprising a terminal alkene group. The reaction is outlined in scheme 2, wherein the denominations are as defined in formula (I).

Scheme 2

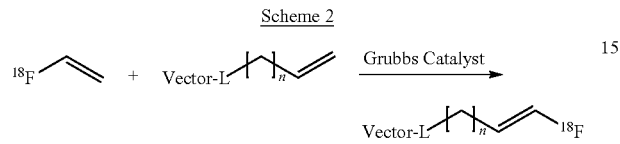

The Grubbs Catalyst has excellent functional group tolerance and readily couple 18F-fluoroethene to the modified vector by means of cross metathesis under release of ethene. In this embodiment of the invention this is used to exchange $^{18}$F-fluoride from $^{18}$F-fluoroethene with a hydrogen of a terminal alkene linked to a vector. Cross metathesis reactions are described e.g. in Org Lett 1999, 1, 1951. For synthetic purposes cross metathesis has found limited use because high yield formation of desired products depends on one reactant being present in large excess. For radiochemistry that will always be the case when $^{18}$F-fluoride is used. The Grubbs Catalyst used is a ruthenium carbenoid, either of the first or second generation. The second generation catalysts are more stable and more active than the original ones. Some examples of relevant catalysts as disclosed by K. Greta, S. Harutyunyan, A. Michrowska, *Angew. Chem. Int. Ed.*, 2002, 114, 4038 are shown below:

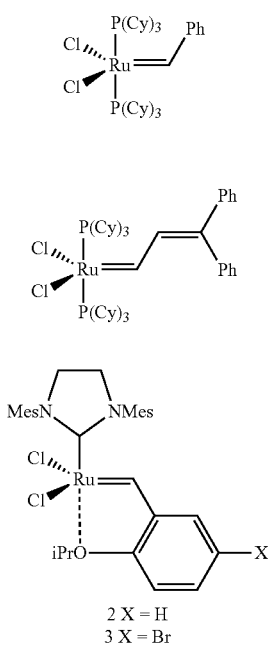

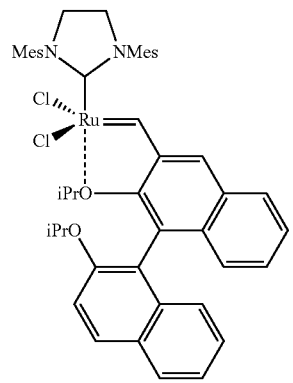

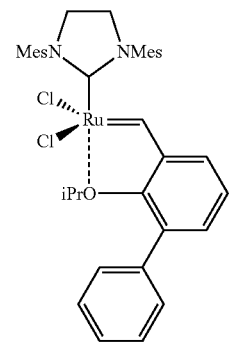

The transalkylidenation of the two alkenes is preferably performed in presence of a anhydrous, aprotic solvent, such as dichloromethane or toluene.

Methods for the preparation of [$^{18}$F]fluoroethene, one of the starting material in the above reaction, have been previously reported by Subramonia et al. (*J. Phys. Chem.*, 1985, 89, 5051; ibid. 1981, 85, 2493) although the presence of by-products may limit the suitability of these methods. $^{18}$F-fluoroethene may also be prepared by a process based on conventional displacement of a leaving group with $^{18}$F$^-$ followed by elimination. The following alternative synthetic routes may be used to prepare $^{18}$F-fluoroethene:

1) By treating $^{18}$F-fluoroethyl comprising a leaving group such as bromide or iodide with palladium under reductive conditions. $^{18}$F-fluoroethyl comprising one leaving group, such as $^{18}$F-fluoroethylbromide, may be prepared by treating a 1,2-disubstituted alkane with $^{18}$F$^-$. In the latter case the alkane is substituted with two leaving groups, of which at least one is either bromide or iodide, and the other can be bromide, iodide, chloride, tosylate, mesylate, triflate or nosylate. The reaction is preferably conducted in the presence of a aprotic polar solvent such as acetonitrile.

2) By treating an $^{18}$F-fluoroethyl comprising a leaving group, e.g. bromide, iodide, chloride, tosylate, mesylate, triflate or nosylate, with a non-nucleophilic base, such as trialkylamine, dimethylpyridine, potassium or sodium tertbutyloxide, sodium hydroxide, potassium hydroxide, carbonate or acetate, or diisopropylamide.

3) By reacting an N,N-dimethyl ethylamine comprising a leaving group, e.g. bromide, iodide, chloride, tosylate, mesylate, triflate or nosylate with $^{18}$F$^-$ and then oxidise the resulting fluoride-N,N-dimethyl ethylamine to the corresponding amino oxide, e.g. with hydrogen peroxide. The resulting amino oxide readily undergoes elimination to form $^{18}$F-fluoroethene. Yet another alternative, is to introduce fluoride to a reagent where the amino oxide is in place changing the order of the sequence.

The alternative synthetic routes discussed above to prepare $^{18}$F-fluoroethene are outlined in scheme 3, wherein X represents a leaving group e.g. selected from Br, I, Cl, OTs, OMs, ONs or OTf. Preferably X is bromide, such that the reactions go via $^{18}$F-fluoroethyl bromide in the first two alternative reactions and bromo-N,N,dimethyl ethylamine is the starting material in the third alternative.

Scheme 3

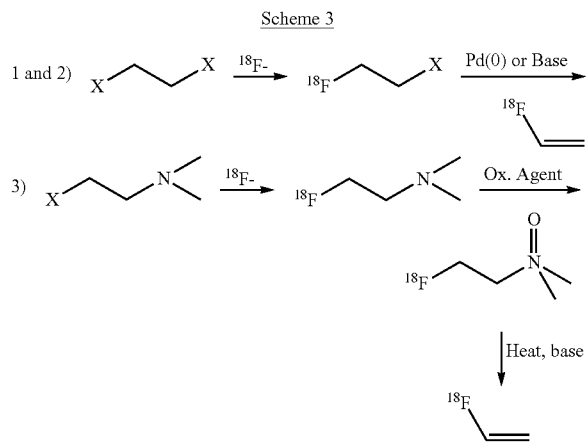

The second starting material in scheme 2, the vector containing a terminal alkene group, may be commercially available or may be prepared using published organic chemistry methods known to the skilled in the art. The methods used in synthesising this will depend on which linker and which vector moieties are used.

In a preferred embodiment, the process for the preparation of the compounds of the invention are carried out in a one-pot tandem reaction wherein $^{18}$F-fluoroethyl comprising a leaving group is added to a solution of palladium(0) and a Grubbs catalyst. This reaction will lead to formation of an alkene and in situ cross metathesis with the Grubbs catalyst will provide a complex wherein the 1-fluoro-ene group is attached to the catalyst. Addition of a vector containing a terminal alkene group will then lead to a second cross metathesis resulting in formation of the compound of the invention. The one-pot tandem reaction is outlined in Scheme 4. The leaving group X is e.g. selected from Br, I, Cl, OTs, OMs, ONs or OTf. The $^{18}$F-fluoroethyl compound is preferably $^{18}$F-fluoroethylbromide. The vector, L and n are defined as in formula (I).

Scheme 4

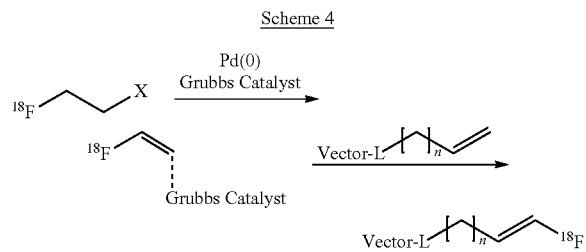

Before use of the compound of the invention, it may be appropriate to formulate it, for example as an aqueous solution by dissolving the compound in sterile isotonic saline which may contain up to 10% of a suitable organic solvent such as ethanol, or a suitable buffered solution such as a phosphate buffer. Other additives may be added such as ascorbic acid to reduce radiolysis. Hence, in a further aspect the present invention also provides a pharmaceutical composition comprising an effective amount, e.g. an amount effective for enhancing image contrast in in vivo PET imaging, of a compound of the invention together with one or more pharmaceutically acceptable adjuvants, excipients or diluents, preferably as an aqueous solution.

Conveniently, the compound of the invention could be provided as part of a kit to a radiopharmacy, PET centre, or nuclear medicine department. The kit may contain a cartridge which can be plugged into a suitably adapted automated synthesiser. The kit includes means for fluorinating with $^{18}$F and may also comprise a column to remove unwanted fluoride ion. The kit preferably includes an appropriate vessel comprising a precursor compound to be $^{18}$F-fluorinated, connected so at to allow the product to be formulated as required. The reagents, solvents and other consumables required for the synthesis may also be included together with a data medium, such as a compact disc carrying the software, which allows the synthesiser to be operated in a way to meet the customer's requirements for radioactive concentration, volumes, time of delivery etc.

Conveniently, all components of the kit are disposable to minimise the possibilities of contamination between runs and may be sterile and quality assured.

In using the kit, a precursor of the compound of the invention, preferably a precursor of a compound of formula (I) would be converted to the compound of the invention by $^{18}$F-fluorination.

In a preferred aspect the invention hence provides a radiopharmaceutical kit for the preparation of a compound according to the invention for use in PET chemistry, which comprises
i) a first vessel containing a precursor of the [$^{18}$F]fluoroalkenylated compound of the invention;
ii) a second vessel with means for eluting the first vessel with $^{18}$F; and optionally
iii) an ion-exchange cartridge for removal of excess $^{8}$F.

The precursor contained in the first vessel is preferably an alkenyl(aryl)iodonium salt of formula (VI).

In a further aspect of the invention, there is provided a method for obtaining a PET image using the compound of the invention. In a preferred embodiment the compound of the invention is used as PET tracers in imaging, diagnosing, for surgical guidance or for monitoring the effect of treatment.

In particular the invention provides a method for obtaining a PET image of a subject comprising:
1) administering to the subject an image-generating amount of a compound of the invention, and
2) measuring the distribution of the compound within the subject by positron emission tomography.

Viewed from a further aspect the invention provides a method for obtaining a PET image of at least a part of a human or animal body, previously administered with a compound of the invention.

Viewed from yet a further aspect the invention provides the use of a compound of the invention for the manufacture of a radiotracer for use in a method for obtaining a PET image involving administration of said radiotracer to a human or animal body and generation of an image of at least part of said body.

The invention is illustrated by way of the following non-limiting examples.

EXAMPLES

Example 1

Synthesis of O-(3-[$^{18}$F]fluoropropenyl)-L-tyrosine

O—[$^{18}$F]fluoroalkenyl)-L-tyrosine as a potential oncologic PET tracer is proposed. The analogous O—[$^{18}$F]fluoroethyl (FET) and O—[$^{18}$F]fluoropropyl-L-tyrosines (FPT) have previously been reported as alternative PET radiotracers to [$^{18}$F]fluoro-2-deoxy-D-glucose (FDG) which unlike FDG, differentiate between tumours and cells associated with inflammation.

Two alternative syntheses of O-(3-[$^{18}$F]fluoropropenyl)-L-tyrosine are presented:

Method 1—Based on Iodonium Chemistry

Starting from the commercially available material N-(tert-butoxycarbonyl)-L-tyrosine methyl ester (1), reaction with 1 equivalent of 3-bromopropyne in the presence of potassium carbonate and acetone yields the O-(1-prop-3-yne)-L-tyrosine (2).

Alkyne reduction to a functionalised terminal alkenyl group is conducted by hydrometallation of 2 with an appropriate boron reagent. Reduction of alkyne 2 to the alkenylboronate pinacol ester 3 is conducted according to the method of Shirakawa et al. (*Synthesis*, 2004, 11, 1814). In the presence of catecholborane and a catalytic amount of dicyclohexylborane (ca. 5 mol %) in tetrahydrofuran at room temperature, the terminal alkyne 2 is reduced to the alkenylboronic acid catechol ester. Subsequent transesterification with pinacol over ca. 24 hours yields the alkenylboronate pinacol ester 3.

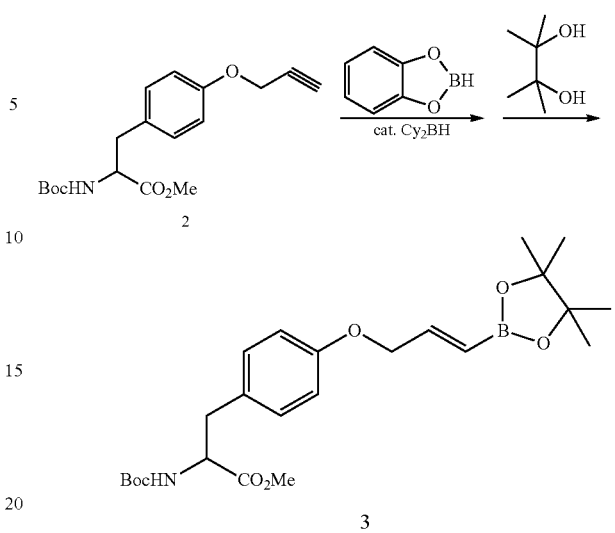

In the presence of 1 equivalent of iodonium transfer reagent Koser's reagent, [hydroxyl(tosyloxy)iodo]benzene, the iodonium salt 4, the precursor for radiolabelling, is prepared from its boronic acid ester in dichloromethane solution. The product iodonium salt 4 is precipitated/crystallised from solution by addition of n-hexane.

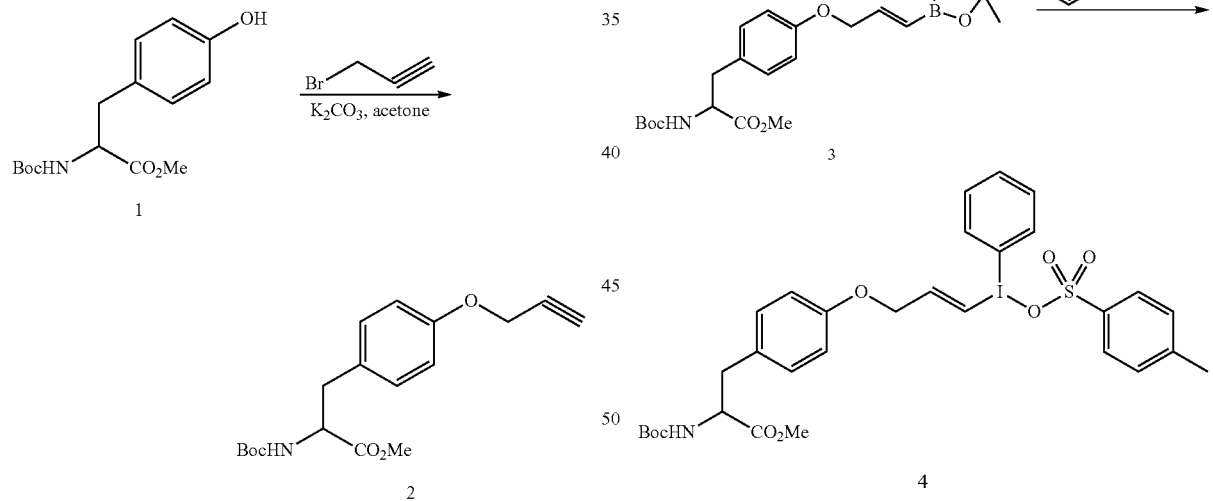

Radiolabelling of 4 with no-carrier-added (nca) [$^{18}$F]fluoride is conducted in a sealed reaction vessel using acetonitrile. The nucleophilic [$^{18}$F]fluoride source is potassium/Kryptofix 222 [$^{18}$F]fluoride. Optimisation of the labelling reaction is conducted by carrying out the radiolabelling at a range of temperatures and different reaction times, e.g. 40 minutes at 90° C.

Finally, deprotection of the amino acid functionality is conducted at high temperature in the presence of HCl followed by chromatographic purification of the O-(3-[$^{18}$F]fluoropropenyl)-L-tyrosine 5 radiolabelled tracer.

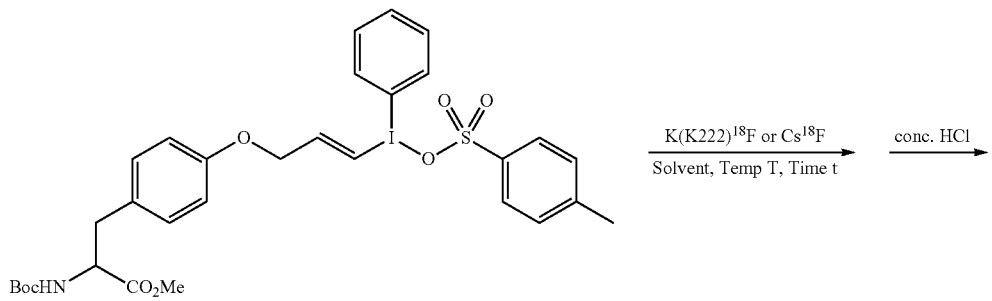

4

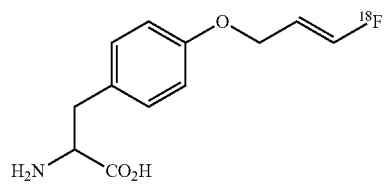

5

Method 2—Based on a Cross Metathesis Reaction

The second labelling strategy described requires the synthesis of [$^{18}$F]fluoroethene. The [$^{18}$F]fluoroethene prepared is used directly in an olefin cross metathesis reaction with Grubbs $1^{st}$ or $2^{nd}$ generation catalysts in the presence of O-(1-prop-3-ene)-L-tyrosine (6) to generate the radiolabelled product O-(3-[$^{18}$F]fluoropropenyl)-L-tyrosine 7. Deprotection of the amino acid functionality results in the preparation of the O-(3-[$^{18}$F]fluoropropenyl)-L-tyrosine radiotracer, 5.

Synthesis of O-(1-prop-3-ene)-L-tyrosine (6)

Starting from the commercially available material N-(tert-butoxycarbonyl)-L-tyrosine methyl ester (1), reaction with 1 equivalent of 3-bromopropene in the presence of a potassium carbonate and acetone yields the O-(1-prop-3-ene)-L-tyrosine (6).

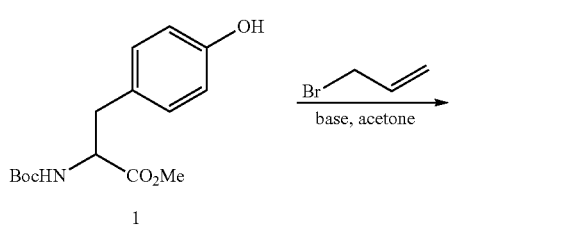

Synthesis of [$^{18}$F]fluoroethene

Starting from commercially available 1,2-dibromoethane, radiolabelling using nca [$^{18}$F]fluoride generates 1-bromo-2-[$^{18}$F]fluoroethane. Radiolabelling of 1,2-dibromoethane with nca [$^{18}$F]fluoride is conducted in a sealed reaction vessel using acetonitrile as solvent. The nucleophilic [$^{18}$F]fluoride source is potassium/Kryptofix 222 [$^{18}$F]fluoride. Optimisation of the labelling reaction is conducted by carrying out the radiolabelling at a range of temperatures and different reaction times.

Introduction of 1-bromo-2-[$^{18}$F]fluoroethane to a solution of tetrakis(triphenylphosphine)palladium(0) in dichloromethane and in the presence of potassium acetate generates [$^{18}$F]fluoroethene. Optimisation of the reaction is carried out by variation of reaction temperatures and times.

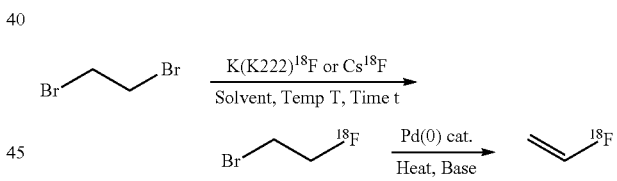

The reaction of [$^{18}$F]fluoroethene, O-(1-prop-3-ene)-L-tyrosine (6) and Grubbs $2^{nd}$ generation catalyst results in the cross-metathesis reaction to generate the O-(3-[$^{18}$F]fluoropropenyl)-L-tyrosine 7. The cross-metathesis reactions are conducted in dichloromethane at temperatures from ambient to reflux over a variety of different reaction times to optimise the reaction conditions.

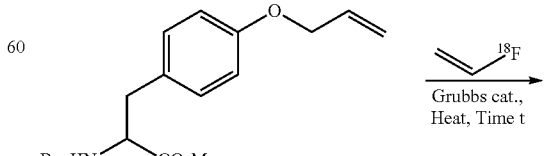

-continued

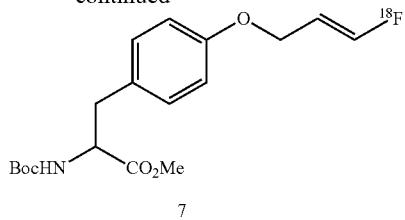

Deprotection of the amino acid functionality of 7 is conducted at high temperature in the presence of HCl followed by chromatographic purification of the O-(3-[$^{18}$F]fluoropropenyl)-L-tyrosine 5 radiolabelled tracer.

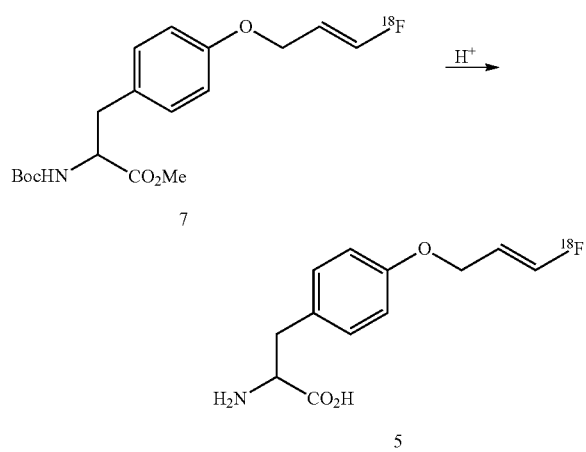

The invention claimed is:

1. A process for the preparation of a compound comprising a [$^{18}$F]fluoroalkenyl group, said method comprising fluorinating an alkenyl(aryl)iodonium salt with $^{18}$F-fluoride.

2. A process as claimed in claim 1 wherein the alkenyl(aryl) iodonium salt is an alkenyl(aryl)iodonium salt of formula (VI),

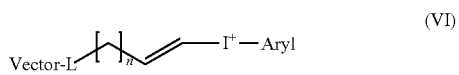

wherein

I$^+$-Aryl represents a phenyliodonium salt, wherein the aryl group is optionally substituted with methoxy, ethoxy, propyloxy, tert-butyloxy, halides or $C_1$-$C_6$-alkyl groups; and n is an integer from 1 to 5;

the vector comprises a moiety having affinity for a biological target; and

L represents a linker moiety.

3. A process as claimed in claim 1 wherein the alkenyl(aryl) iodonium salt is prepared by
   i) reacting a vector moiety, optionally comprising a protecting group, with an alkyne to prepare a compound comprising a vector moiety linked to an alkyne group;
   ii) hydrometalating the alkyne group of the compound from step (i) to prepare a metalated alkene;
   iii) reacting the metalated alkene of step (ii) with an iodonium transfer reagent to prepare the alkenyl(aryl)iodonium salt.

4. A process as claimed in claim 3 optionally followed by
   a) removal of excess $^{18}$F; and/or
   b) removal of any protecting groups; and/or
   c) removal of organic solvents; and/or
   d) formulation of the resultant $^{18}$F-labelled compound as an aqueous solution.

5. A process for preparation of a compound comprising a [$^{18}$F]fluoroalkenyl group, said method comprising cross metathesis reacting a $^{18}$F-fluoroethene with a compound comprising a terminal alkene group in the presence of a Grubbs catalyst.

6. A process as claimed in claim 5 carried out in a one-pot tandem reaction wherein a $^{18}$F-fluoroethyl comprising a leaving group is added to a solution of palladium(0) and a Grubbs catalyst to prepare $^{18}$F-fluoroethene, followed by addition of a compound comprising a terminal alkene group.

7. A process as claimed in claim 5 wherein the compound comprising a terminal alkene group is a vector moiety comprising a terminal alkene group.

* * * * *